(12) United States Patent
Foley et al.

(10) Patent No.: US 7,655,042 B2
(45) Date of Patent: Feb. 2, 2010

(54) EXPANDABLE INTERVERTEBRAL SPACERS

(75) Inventors: Kevin Foley, Germantown, TN (US);
Harald Ebner, Deggendorf (DE);
Mingyan Liu, Bourge la Reine (FR);
Charles Branch, Advance, NC (US);
Lawrence M. Boyd, Memphis, TN (US)

(73) Assignee: Warsaw Orthopedic, Inc.

( * ) Notice: Subject to any disclaimer, the term of this patent is extended or adjusted under 35 U.S.C. 154(b) by 0 days.

(21) Appl. No.: 10/999,727

(22) Filed: Nov. 30, 2004

(65) Prior Publication Data

US 2005/0113920 A1  May 26, 2005

Related U.S. Application Data

(62) Division of application No. 10/155,483, filed on May 23, 2002, now Pat. No. 6,833,006, which is a division of application No. 09/691,307, filed on Oct. 18, 2000, now Pat. No. 6,395,031, which is a division of application No. 09/182,560, filed on Oct. 29, 1998, now Pat. No. 6,193,757.

(51) Int. Cl.
*A61F 2/44* (2006.01)

(52) U.S. Cl. .................................................. 623/17.11

(58) Field of Classification Search .... 623/17.11–17.16
See application file for complete search history.

(56) References Cited

U.S. PATENT DOCUMENTS

| | | | |
|---|---|---|---|
| 3,875,595 A | 4/1975 | Froning | |
| 4,309,777 A | 1/1982 | Patil | |
| 4,401,112 A | 8/1983 | Rezain | |
| 4,553,273 A | 11/1985 | Wu | |
| 4,554,914 A | 11/1985 | Kapp et al. | |
| 4,636,217 A | 1/1987 | Ogilvie et al. | |
| 4,759,769 A * | 7/1988 | Hedman et al. | 623/17.13 |
| 4,863,476 A * | 9/1989 | Shepperd | 623/17.15 |
| 4,863,477 A | 9/1989 | Monson | |
| 4,911,718 A | 3/1990 | Lee et al. | |
| 4,932,975 A | 6/1990 | Main et al. | |
| 4,997,432 A | 3/1991 | Keller | |
| 5,059,193 A | 10/1991 | Kuslich | |
| 5,062,850 A | 11/1991 | MacMillan et al. | |

(Continued)

FOREIGN PATENT DOCUMENTS

DE    4012622 C1    7/1991

(Continued)

OTHER PUBLICATIONS

J.A.N. Shepperd, "Intervertebral Implants for Fixation and Disc Replacement".

*Primary Examiner*—David J Isabella
*Assistant Examiner*—Ann Schillinger

(57) ABSTRACT

Laterally expanding vertebral spacer devices are provided for repairing damaged vertebral discs. The vertebral spacer devices maintain the height of a distracted vertebral disc space while providing stability to the spine. In one form of the invention, a vertebral spacer device is provided with a first arm movably coupled to a second arm. The first and second arms are laterally expandable from a first width for insertion into the disc space to a second width after insertion into the disc space. The first and second arms also define a cavity therebetween for placement of bone growth material.

29 Claims, 11 Drawing Sheets

U.S. PATENT DOCUMENTS

| | | | |
|---|---|---|---|
| 5,123,926 A | | 6/1992 | Pisharodi |
| 5,171,278 A | * | 12/1992 | Pisharodi .................... 128/898 |
| 5,236,460 A | | 8/1993 | Barber |
| 5,258,031 A | | 11/1993 | Salib et al. |
| 5,263,953 A | | 11/1993 | Bagby |
| 5,290,312 A | | 3/1994 | Kojimoto et al. |
| 5,306,310 A | | 4/1994 | Siebels |
| 5,314,477 A | | 5/1994 | Marnay |
| 5,336,223 A | | 8/1994 | Rogers |
| 5,360,430 A | | 11/1994 | Lin |
| 5,390,683 A | | 2/1995 | Pisharodi |
| 5,391,168 A | * | 2/1995 | Sanders et al. ................ 606/61 |
| 5,397,364 A | | 3/1995 | Kozak et al. |
| 5,423,817 A | | 6/1995 | Lin |
| 5,458,642 A | | 10/1995 | Beer et al. |
| 5,507,816 A | | 4/1996 | Bullivant |
| 5,522,899 A | | 6/1996 | Michelson |
| 5,534,030 A | | 7/1996 | Navarro et al. |
| 5,549,679 A | | 8/1996 | Kuslich |
| 5,554,191 A | * | 9/1996 | Lahille et al. ........... 623/17.11 |
| 5,556,431 A | | 9/1996 | Buttner-Janz |
| 5,609,635 A | | 3/1997 | Michelson |
| 5,616,142 A | | 4/1997 | Yuan et al. |
| 5,645,599 A | | 7/1997 | Samani |
| 5,653,763 A | * | 8/1997 | Errico et al. ............. 623/17.11 |
| 5,658,335 A | | 8/1997 | Allen |
| 5,665,122 A | | 9/1997 | Kambin |
| 5,674,294 A | | 10/1997 | Bainville et al. |
| 5,676,702 A | | 10/1997 | Ratron |
| 5,693,100 A | | 12/1997 | Pisharodi |
| 5,702,391 A | | 12/1997 | Lin |
| 5,702,450 A | * | 12/1997 | Bisserie .................... 623/17.16 |
| 5,713,904 A | | 2/1998 | Errico et al. |
| 5,749,916 A | | 5/1998 | Richelsoph |
| 5,782,832 A | | 7/1998 | Larsen et al. |
| 5,800,547 A | | 9/1998 | Schafer et al. |
| 5,865,845 A | | 2/1999 | Thalgott |
| 5,865,847 A | | 2/1999 | Kohrs et al. |
| 5,865,848 A | | 2/1999 | Baker |
| 5,928,284 A | | 7/1999 | Mehdizadeh |
| 5,976,187 A | | 11/1999 | Richelsoph |
| 5,980,522 A | | 11/1999 | Koros et al. |
| 5,989,291 A | * | 11/1999 | Ralph et al. ............. 623/17.15 |
| 6,001,130 A | | 12/1999 | Bryan et al. |
| 6,019,793 A | * | 2/2000 | Perren et al. ............. 623/17.16 |
| 6,039,761 A | * | 3/2000 | Li et al. ................... 623/17.16 |
| 6,045,579 A | * | 4/2000 | Hochshuler et al. ...... 623/17.16 |
| 6,080,193 A | | 6/2000 | Hochshuler et al. |
| 6,117,174 A | * | 9/2000 | Nolan ..................... 623/17.11 |
| 6,126,689 A | * | 10/2000 | Brett ....................... 623/17.16 |
| 6,179,875 B1 | * | 1/2001 | Von Strempel ........... 623/17.16 |
| 6,193,757 B1 | | 2/2001 | Foley et al. |
| 6,206,923 B1 | * | 3/2001 | Boyd et al. .............. 623/17.11 |
| 6,224,631 B1 | | 5/2001 | Kohrs |
| 6,258,125 B1 | | 7/2001 | Paul et al. |
| 6,309,421 B1 | | 10/2001 | Pisharodi |
| 6,371,989 B1 | | 4/2002 | Chauvin et al. |
| 6,395,031 B1 | | 5/2002 | Foley et al. |
| 6,491,724 B1 | * | 12/2002 | Ferree ..................... 623/17.11 |
| 2001/0034553 A1 | * | 10/2001 | Michelson ............... 623/17.11 |

FOREIGN PATENT DOCUMENTS

| | | |
|---|---|---|
| DE | 43 23 595 C1 | 7/1993 |
| DE | 4328690 A1 | 3/1995 |
| DE | 44 16 605 | 6/1995 |
| DE | 19826619 | 6/1998 |
| EP | 0 188 954 A1 | 12/1985 |
| EP | 0 260 044 A1 | 8/1987 |
| EP | 0 346 269 A2 | 6/1989 |
| EP | 0 566 810 A1 | 4/1992 |
| EP | 0 610 837 A1 | 2/1994 |
| GB | 2 207 607 A | 2/1989 |
| WO | WO 90/11740 | 10/1990 |
| WO | WO 92/14423 | 9/1992 |
| WO | WO 95/00082 | 1/1995 |
| WO | WO 95/15133 | 6/1995 |
| WO | WO 9531158 | 11/1995 |
| WO | WO 96/14809 | 5/1996 |
| WO | WO 97/00054 | 1/1997 |
| WO | WO 97/15246 | 5/1997 |
| WO | WO 97/15247 | 5/1997 |
| WO | WO 97/31517 | 8/1997 |
| WO | WO 98/14142 | 4/1998 |
| WO | WO 98/34568 | 8/1998 |
| WO | WO 98/48739 | 11/1998 |
| WO | WO 99/32054 | 7/1999 |
| WO | WO 99/42062 | 8/1999 |

* cited by examiner

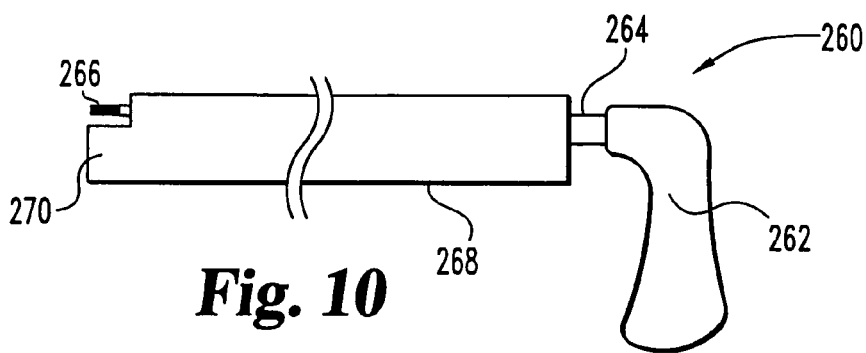
*Fig. 10*
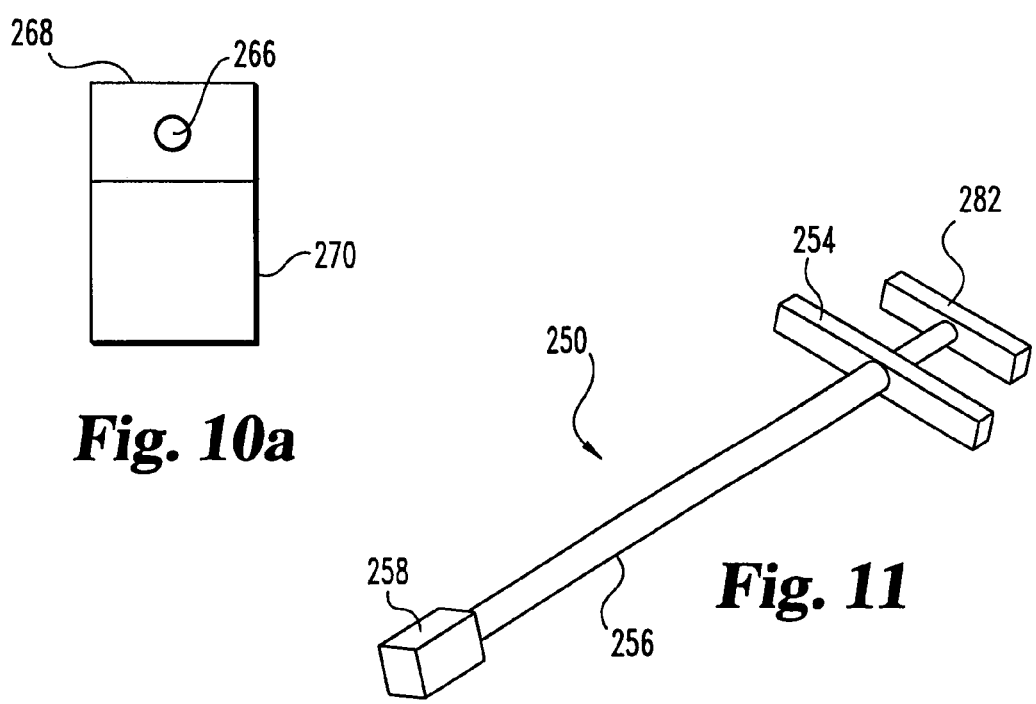
*Fig. 10a*
*Fig. 11*
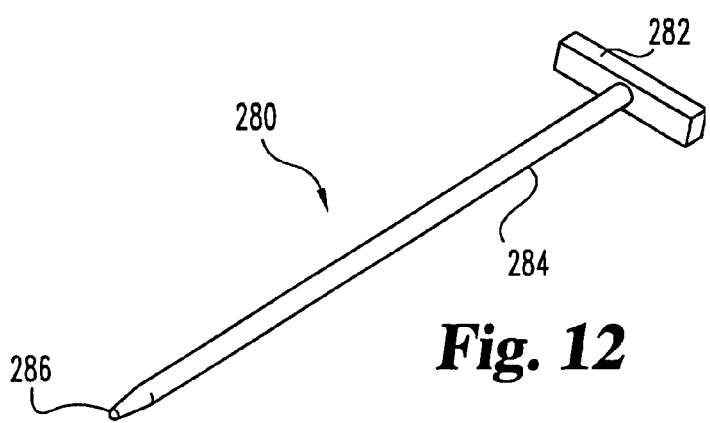
*Fig. 12*

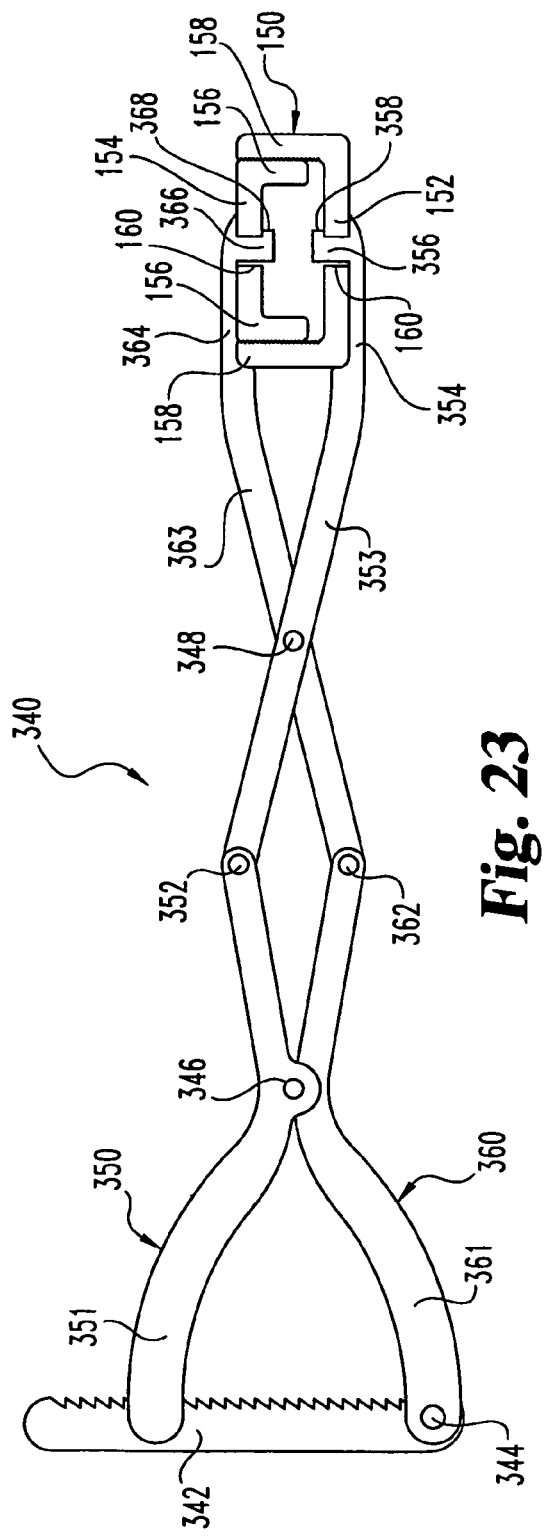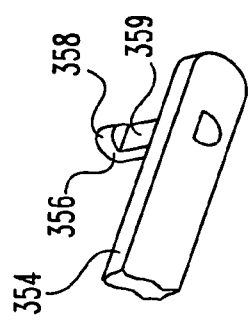
Fig. 23
Fig. 23a

EXPANDABLE INTERVERTEBRAL SPACERS

REFERENCE TO RELATED APPLICATIONS

This application is a divisional of U.S. patent application Ser. No. 10/155,483, filed May 23, 2002, now U.S. Pat. No. 6,833,006, which is a divisional of U.S. patent application Ser. No. 09/691,307, filed Oct. 18, 2000, now U.S. Pat. No. 6,395,031, which is a divisional of U.S. patent application Ser. No. 09/182,560, filed Oct. 29, 1998, now U.S. Pat. No. 6,193,757, all of which are incorporated by reference in their entirety.

BACKGROUND

The present invention is directed to implantable devices for stabilizing the spine. Specifically, the invention concerns intervertebral spacers expandable from a reduced size insertion configuration to an expanded size spacing configuration.

Intervertebral discs, located between the end plates of adjacent vertebrae, stabilize the spine, distribute forces between vertebrae and cushion vertebral bodies. An intervertebral disc may deteriorate due to trauma, aging or disease resulting in pain or discomfort to a patient. One common procedure for relief of patient discomfort is a discectomy, or surgical removal of a portion or all of an intervertebral disc. Often, this is followed by implantation of a device between adjacent vertebrae to maintain or restore disc space height. Typically, implantation of such a device is also intended to promote bony fusion between the adjacent vertebral bodies.

One limitation on the size of a device inserted into the disc space is the size of the opening through surrounding tissue that is available to gain access to the disc space. From a posterior approach to the spine, the dura and nerve roots must be mobilized to gain access to the disc space. Similarly, from an anterior approach, the aorta and vena cava must be mobilized to gain access to the disc space. Such mobilization is often limited by the anatomical structures, thus resulting in a relatively small access site. Removal of additional bone to enlarge an entrance to the disc space may weaken the joint between two adjacent vertebra. Moreover, excessive retraction of vessels and neural structures to create a large access opening may damage these tissues. Thus, prior procedures have been limited to placing a first device passable through the available opening on one side of the spine and mobilizing the tissue or vessels to place another similar implant on the opposite side of the spine. Each implant being limited in size by the available access site.

Thus, there remains a need for implantable devices that have a reduced size insertion form and are expandable in the disc space to a larger size for enhancing spine stability and facilitating immobilization via bony fusion.

SUMMARY

The present invention contemplates an intervertebral spacer device that has a reduced size configuration for insertion into a disc space and an expanded size configuration to maintain the spacing of the disc space. In one aspect of the present invention, the device includes a pair of arms each having a first end and a second end, the arms being movably coupled at their first ends. When the arms are positioned adjacent one another, the device is in a reduced size configuration for insertion into the disc annulus. The device is laterally expandable in the disc space to an expanded configuration by moving the pair of arms about the first ends in order to increase the dimension of the device perpendicular to the longitudinal axis of the spine while maintaining the interspace distraction. Preferably, the expanded device creates a cavity that may be filled with bone or bone substitute material for purposes of promoting fusion between the adjacent vertebrae. Preferably, the height of the device in the reduced size configuration is substantially the same as the height in the expanded configuration, with the expanded configuration providing an increased base of support.

In another embodiment of the present invention, the first and second arms each have laterally extending portions extending therefrom that cooperate to engage the first and second arms to one another. Preferably, each of the laterally extending portions defines a plurality of serrations, wherein the serrations of one laterally extending portion of the first arm cooperate in interdigiting fashion with serrations of the corresponding laterally extending portion of the second arm. In one preferred embodiment, the laterally extending portions are provided at the first and second ends of each of the arms. In another preferred embodiment, the pair of arms are pivotably coupled at their first ends, and laterally extending portions are provided at the second ends.

In still a further embodiment, the pair of arms are flexibly attached such that they are compressible into a first smaller configuration and laterally self-expand to a second larger configuration. In one such embodiment, the arms are interconnected by a flexible hinge portion at one end of each arm. In another embodiment, each arm is flexibly connected to a first end portion and an opposing second end portion to form a substantially rectangular shape having flexible side walls. Preferably, the side walls are biased to assume the second larger configuration.

In another aspect, a vertebral spacer device is provided that is capable of insertion in a smaller form and laterally expandable within the disc space to an enlarged configuration for supporting the spine.

Other objects and advantages of the present invention will be readily discerned upon consideration of the following written description and accompanying figures.

BRIEF DESCRIPTION OF THE DRAWINGS

FIG. 10 is a side view of an insertion tool useable with the vertebral spacer devices of the present invention.

FIG. 10a is an end view of the insertion tool of FIG. 10.

FIG. 11 is a perspective view of an expansion tool useable with the vertebral spacer devices of the present invention.

FIG. 12 is a perspective view of an element of FIG. 11.

FIG. 19c is a side view of the implant of FIG. 19a.

FIG. 23 is a plan view of an expansion tool usable with the vertebral spacers of FIGS. 20-23.

FIG. 23a is a fragmentary perspective view of a portion of the insertion tool device of FIG. 23.

DESCRIPTION OF SELECTED EMBODIMENTS

Figure 1:
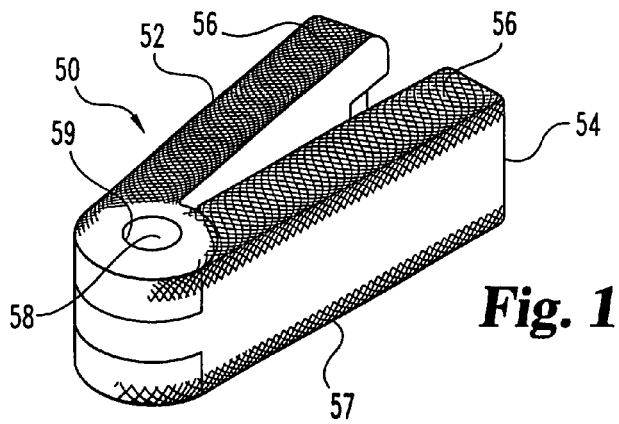
FIG. 1. is a perspective view of one embodiment of a vertebral spacer device according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated devices, and any further applications of the principles of the invention as illustrated therein being contemplated as would normally occur to one skilled in the art to which the invention relates.

In accordance with one embodiment of the invention, a vertebral spacer device 50 is depicted in FIGS. 1-6. Device 50 includes a first lateral arm 52 and a second lateral arm 54. First arm 52 includes a first end 60 and an opposite connection end 61. Second arm 54 includes a first end 62 and an opposite connection end 63. First arm connection end 61 is fixedly coupled to second arm connection end 63 via connection pin 58 extending through a bore 59 defined through connection ends 61 and 63. Bore 59 extends transverse to the longitudinal axis 53 of spacer 50.

Figure 6:
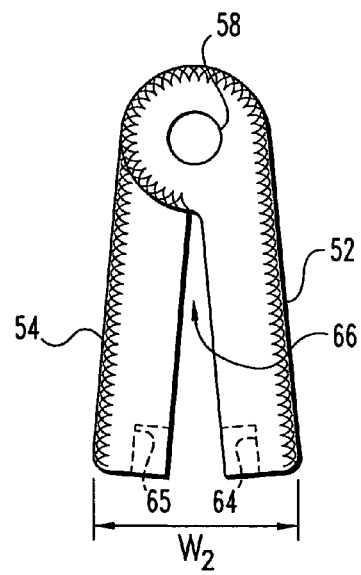
FIG. 6 is a top view of the vertebral spacer of FIG. 1 shown in an expanded position.

First arm 52 and second arm 54 each define a portion of a top bone engaging surface 56 adapted to engage a vertebral body and a portion of bottom bone engaging surface 57 substantially identical to top bone engaging surface 56. When first arm 52 and second arm 54 are in an opened position, as shown in FIG. 6, a central cavity 66 is defined therebetween. Cavity 66 is adapted to receive a graft or bone-growth inducing material therein.

Referring now to FIGS. 3-6, the vertebral spacer device 50 is illustrated and described below in further detail. Connection end 63 of second arm 54 is fixedly coupled to connection end 61 of first arm 52 via connection pin 58 extending through bore 59. However, it should be understood that any type of connection mechanism contemplated herein, provide the principles of the current invention are adhered to. As an example, but without limitation, an alternative connection mechanism may be a hinge between and fixedly engaging first arm 52 and second arm 54 to allow pivotal movement therebetween. Alternatively, first and second arms may be integrally formed of a flexible material, thereby permitting movement at the connection point.

Figure 4:
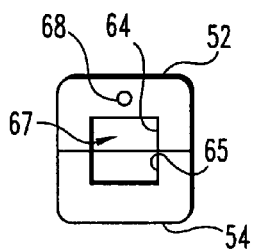
FIG. 4 is a right end view of the vertebral spacer device of FIG. 2.
Figure 5:
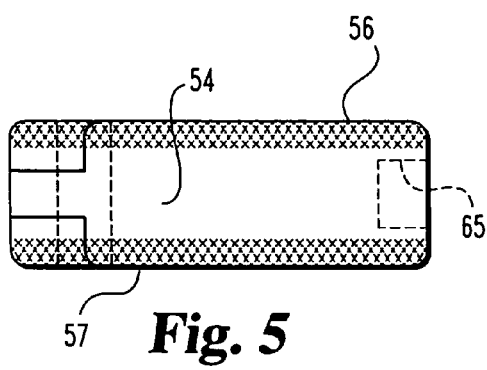
FIG. 5 is an elevational view of the vertebral spacer device of FIG. 2.

First end 60 of first arm 52 and first end 62 of second arm 54 each define a corresponding socket portion 64 and 65, respectively. When device 50 is in a first closed position, as shown in FIG. 4, socket portions 64 and 65 define a socket for 67 for receiving a driving tool, which will be described more fully below. End 60 also includes an internally threaded bore 68 defined by device 50. Threaded bore 68 is provided to receive an attachment portion of an insertion tool configured for manipulation of device 50 into and out of a disc space.

It should be noted that in the illustrated embodiment first arm 52 and second arm 54 are configured such that the top bone engaging surface 56 defined on each of the arms 52 and 54 extends in a substantially uniform horizontal plane to make the bone engaging surface 56 substantially planar in a first plane. The bottom bone engaging surface 57 defined by arms 52 and 54 also extends in a substantially uniform horizontal plane making the bottom bone engaging surface 57 substantially planer in a second plane. In a preferred embodiment, the first and second planes are generally parallel and separated by a height. Preferably, the height between the first and second planes is substantially constant between the closed position of FIG. 2 and the open positions of FIGS. 6 and 9. Thus, the disc space height during insertion may be substantially maintained in the expanded position.

Figure 2:
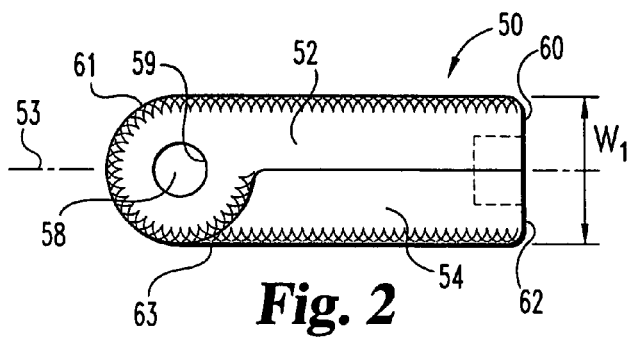
FIG. 2 is a top view of the vertebral spacer device of FIG. 1.
Figure 3:
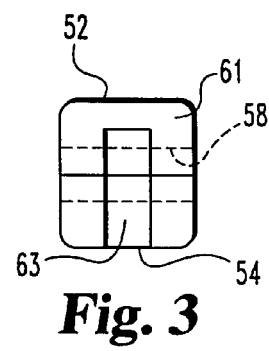
FIG. 3 is a left end view of the vertebral spacer device of FIG. 2.

Device 50 may be positioned in a closed position forming a reduced size configuration shown in FIGS. 2-4. Preferably, arms 52 and 54 are closely adjacent in this position, although the exact arm positioning may vary depending on the application. In the closed position, device 50 has a lateral width WI extending transverse to longitudinal axis 53 of the device.

Figure 9A:
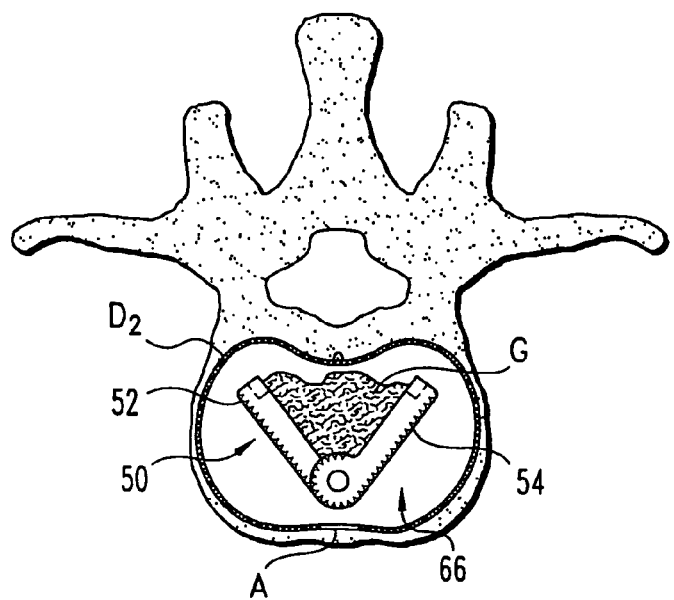
FIG. 9a is a partial cross-sectional top view of the vertebrae of FIG. 8 with the vertebral spacer device of FIG. 1 in an expanded position between the vertebrae.

Device 50 may be positioned in an open position forming an expanded size configuration as shown in FIGS. 1, 6 and 9. The extent of distance between first arm 52 and second arm 54 may be varied depending on the expanded size desired. In the open position, device 50 may have at least a lateral width $W_2$ extending transverse to longitudinal axis 53 of the device. Lateral width $W_2$ being greater than lateral width $W_1$. As shown in FIG. 9a, the lateral width in the expanded configuration may be substantially greater than width $W_1$. This expanded width provides a much wider base of support than the device does in the closed position. The wider base of support provides greater stability of the device.

Figure 9B:
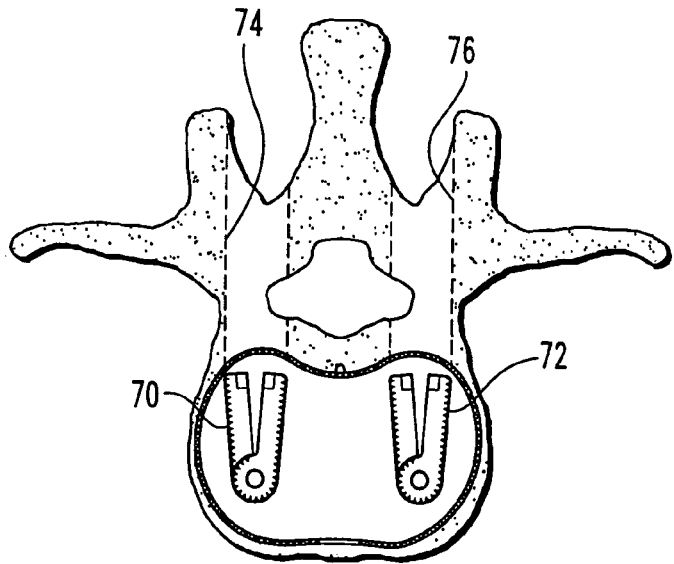
FIG. 9b is a partial cross-sectional top view of a vertebral body as shown in FIG. 8, with a pair of vertebral spacer devices according to FIG. 1 inserted from a bilateral posterior approach.

Referring to FIG. 9b, there is shown a vertebral body with two laterally expandable implants according to the present invention. Implants 70 and 72, slightly smaller versions of device 50, have been inserted through posterior openings 74 and 76, respectively, into the disc space in their reduced size insertion form. It will be understood that this placement is approximately in the same position in the disc space into which known devices may be placed. In much the same manner that chairs, such as tall stools, are subject to tipping if the legs are too close, implants may also be subject to tipping if they lack a sufficiently wide base support area. However, referring to FIG. 9c, the present invention permits each of devices 70 and 72 to be expanded in the disc space to a greater width, thereby increasing the total width of the base of support. Moreover, material G promoting bone growth may be placed in the cavity between the arms and around the exterior of the implants.

The bone engaging surfaces 56 and 57 of device 50 are configured to provide an even distribution and transfer of the load from the upper vertebral body through the integral side walls of device 50 to the lower vertebral body. In a preferred embodiment, the endface plates 56 and 57 are knurled to provide frictional engagement between the vertebrae and the device 50. While knurling is shown as one configuration for the bone engaging surface, other configurations may be utilized. For example, but without limitation, grooves may be formed on the upper and lower bone engaging surfaces extending transverse to longitudinal axis 53 to resist expulsion. More specifically, arcuate grooves may be formed having a radius of curvature originating at pin 58 to follow the arc of the arms as they are expanded in the disc space to form the expanded open position shown in FIG. 6.

Figure 7:
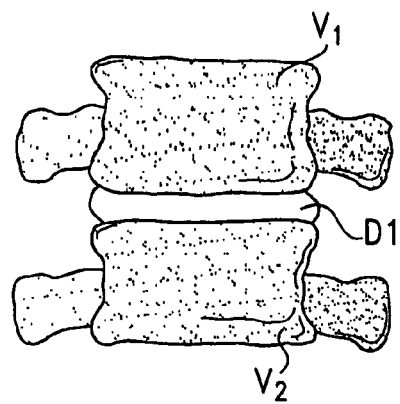
FIG. 7 is an anterior-posterior view of a pair of vertebrae having a collapsed disc space therebetween.
Figure 8:
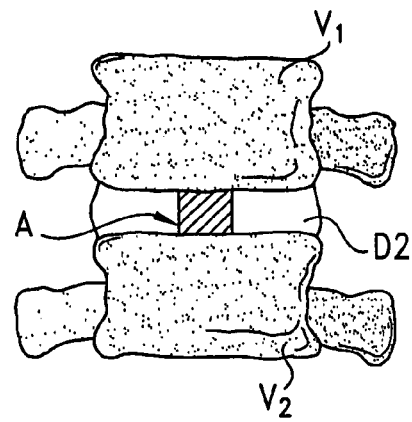
FIG. 8 is an anterior-posterior view of the vertebrae of FIG. 7 showing the vertebrae after distraction of the disc space.

Referring to FIGS. 7-9, a spinal segment with vertebrae $V_1$ and $V_2$ is illustrated to briefly describe a surgical procedure in which device 50 may be employed. More specifically, in FIG. 7 a damaged or diseased spinal segment is shown without the device 50. D1 represents a degenerated or damaged disc between vertebrae $V_1$ and vertebrae $V_2$ that has resulted in the collapse of the disc space between the vertebrae. Vertebrae $V_1$ and $V_2$ form part of a spinal column having a longitudinal axis L extending therethrough.

In FIG. 8, the vertebrae $V_1$ and $V_2$ are shown distracted such that the disc space is restored to approximately its normal height, represented by distracted disc space D2. Tensioning of annular structures that extend between D1 and D2 promotes disc stability. Also shown is an opening A made in the annulus fibrosus that may be created by the surgeon by an annulotomy or disectomy surgical procedure to gain access to the disc space from an anterior approach. As known in the art and not further described herein, the adjacent end plates of $V_1$ and $V_2$ may be prepared to promote bone fusion therebetween and accept device 50. Device 50 is inserted through opening A while in the reduced size configuration (as shown in FIGS. 2 through 4). Once inserted into the disc space, the device 50 is laterally expanded to expanded size configuration (as shown in FIGS. 1 and 6) by moving first arm 52 in relation to second arm 54 in the disc space. The lateral expansion of device 50 increases the lateral dimension of device 50 in a direction transverse to longitudinal axis L, while maintaining the height of distracted disc space D2. In FIG. 9 the device 50 is shown in plan view inserted into D2 between vertebrae $V_1$ and $V_2$ through opening A. It will be understood that use of the laterally expandable implant according to the present invention limits the amount of mobilization of overlapping vessels and permits insertion of an implant having a much wider spacing configuration than would otherwise be implantable with a non-expanding implant.

The expanded configuration of device 50 creates cavity 66 that may then be filled with a bone graft material or bone-growth inducing material G for the purposes of promoting fusion between vertebrae $V_1$ and $V_2$. The graft material G also helps to maintain the device 50 in the laterally expanded configuration. As can be seen in FIG. 9, the expanded device 50 is larger than the opening A made through the annulus fibrosus. Thus, in addition to the knurled endface plates 56 and 57, the remaining annulus fibrosis may also act to limit displacement of device 50 from the disc space. While the device has been inserted with the wider end adjacent opening A, it is contemplated that the connection end may be disposed adjacent the opening. For this use, a biasing element, such as a spring, may be disposed between the arms to urge them to the expanded condition.

FIGS. 7-9c illustrate two methods for inserting laterally expandable devices into the disc space D2. The present invention also contemplates the use of additional methods as known in the art for inserting interbody fusion implants. For example, more than one vertebral spacer device may be inserted through the same opening A. For example, a first device 50 could be inserted and laterally expanded, and packed with bone graft material. Then a second device may be inserted in the disc space and between the arms of the first device. The second device may be laterally expanded and packed with bone graft material G.

Figure 9C:
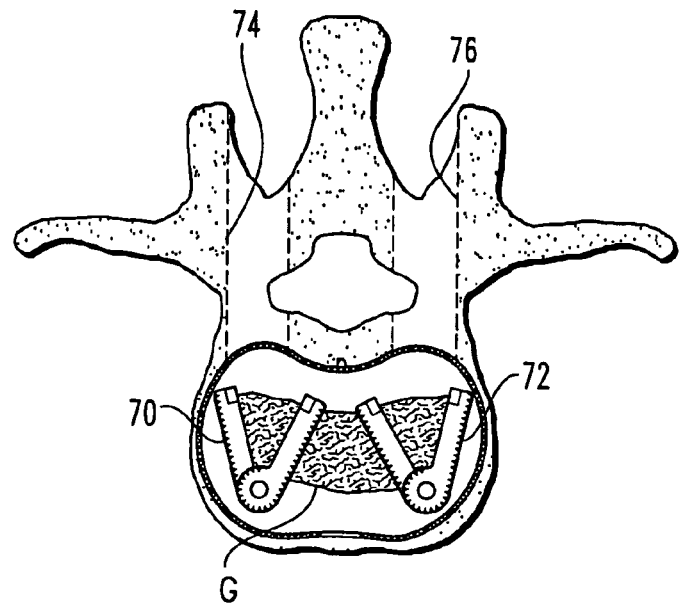
FIG. 9c shows the vertebral spacer devices of FIG. 9b in an expanded configuration.

Referring to FIGS. 9a and 9b, there is shown a vertebral body with two implants positioned in the disc space. In this procedure, bilateral access to the disc space is achieved by posterior openings 74 and 76. It will be understood that the size of openings may be limited by the amount of dural compression that may be safely achieved, nerve root location and the amount of bone removed adjacent the disc space. Devices 70 and 72 are inserted via opening 74 and 76, respectively. The devices are inserted into the disc space in the reduced size configuration. Once disposed in the disc space, devices 70 and 72 are expanded and graft material is positioned in the cavity formed between the arms. Preferably, as shown in FIG. 9c, material may be positioned between the implants before one or both are expanded to provide a further area for bone growth. While a device according to FIG. 1 has been shown for the purposes of illustrating the methods of insertion, it is contemplated that the other embodiments disclosed herein may be inserted in a like manner.

Referring now to FIGS. 10-12, various instruments useful for insertion and lateral expansion of device 50 are shown therein. The insertion tool 260 of FIG. 10 is useable for insertion of device 50 into the disc space. Insertion tool 260 includes a handle portion 262, a threaded stem portion 266, and rod 264 extending between handle 262 and threaded portion 266. A sleeve 268 is slidably disposed about the stem 264. Sleeve 268 includes protrusion 270 extending therefrom and adapted to engage cavity 67 in device 50. While not illustrated, device 260 may include a stop mechanism operable to prevent sliding of sleeve 268 about rod 264 after device 50 is engaged thereto.

To use insertion tool 260 to insert the implant device 50, threaded portion 266 threadedly engages device 50 via threaded bore 68. Once the device 50 is threadedly engaged to insertion tool 260, sleeve 268 may be slid down rod 264 toward the device 50 until protrusion 270 resides within cavity 67. Rod 264 and protrusion 270 prevent rotation between device 50 and insertion tool 260 during insertion. The vertebral spacer device 50 may then be inserted into a prepared disc space using the insertion tool 260. Once device 50 is placed in the disc space, sleeve 268 may be retracted towards handle 262 to disengage protrusion 270 from cavity 67. Threaded stem portion 266 may then be removed from threaded bore 68. Alternatively, if it is desired to remove the device 50 from the disc space after initial insertion or to reposition the device 50 within the disc space, the threaded stem portion 266 allows the device 50 to be withdrawn or repositioned. It is contemplated herein that insertion of device 50 into the disc space via insertion tool 260 is accomplished with device 50 in a closed position, as shown in FIG. 2.

Once the device 50 is inserted into the desired position in the disc space, first arm 52 and second arm 54 may be laterally expanded to increase the lateral dimension of device 50 with respect to spinal longitudinal axis L in order to stabilize the spinal column and fill a larger portion of the disc space. In a preferred embodiment, each bone engaging surface 56 and 57 includes a beveled edge around the perimeter of device 50. The beveled edge facilitates insertion between adjacent vertebrae and eases expansion in the disc space.

FIG. 11 illustrates one type of driving tool 250 operable to at least initially laterally expand device 50 to a laterally expanded configuration. Driving tool 250 includes T-handle portion 254, a square driving end 258 adapted to engage cavity 67, and a hollow tube 256 extending between handle portion 254 and driving end 258. In order to laterally expand device 50, driving tool 250 is rotated via the T-handle 254 with driving end 258 disposed within cavity 67. Rotation of driving end 258 causes first arm 52 and second arm 54 to move laterally with respect to one another in a manner that laterally expands the arms 52 and 54 of device 50.

In order to further laterally expand first arm 52 and second arm 54, a spreader 280 as shown in FIG. 12 may be used in conjunction with tool 250. Spreader 280 includes a first end 282, a wedge portion 286, and stem 284 extending therebetween. As shown in FIG. 11, spreader 280 may be disposed within hollow tube 256 and advanced beyond its distal end to more fully expand the device. Wedge portion 286 may be placed between first arm 52 and second arm 54. A force applied to first end 282 drives wedge portion 286 between arms 52, 54 in order to further laterally expand the device 50.

While the above-described spreader is disclosed as a preferred embodiment, it is contemplated that other instruments may be used to expand the device without deviating from the scope of the invention. Specifically, spreader 280 may be used may be used alone to laterally spread the expandable device.

As shown in FIGS. 6 and 9, when device 50 is in a laterally expanded position, a cavity 66 is formed between first arm 52 and second arm 54. A graft material G may then be placed or packed into cavity 66. The graft material G could be cancellous bone or bone chips, or a suitable bone graft substitute material known to those skilled in the art. One advantage of the device 50 is that it allows bone graft material G to be placed at or near the central portion of the vertebrae while the expandable spacer engages more lateral portions of the vertebra. This central portion is known to be highly vascular and biologically active, so that it is an excellent location for bone graft incorporation and fusion. In addition, bone-growth enhancing materials may be introduced with the graft material to enhance initial and ultimate fusion of the vertebrae $V_1$ and $V_2$.

It should be appreciated that device 50 may be delivered to the disc space for insertion through a cannula employed in a minimally-invasive surgical technique. Device 50 is sized for placement through the cannula in its unexpanded configuration. Once positioned in the disc space, the lateral dimension of the device is increased by expanding the first and second arms 52, 54 as described above. Other surgical techniques for insertion are contemplated, for example, open surgical procedures with direct access to the spine. Device 50 thus allows minimization of the size of the entry into the disc space and the resulting damage to tissue surrounding the surgical site. Further, the reduced size configuration of the implant permits insertion of a relatively large spacer where anatomical features, such as the dura, nerve roots or blood vessels, would have prevented placement of a larger, non-expanding sized spacer.

Referring now to FIGS. 13-16, another embodiment of the present invention is illustrated. The expandable vertebral spacer 80 includes a first arm 82 having a distal end 90, and a second arm 84. Second arm 84 is movable coupled to main body portion 82 via hinge portion 98. First arm 82 is provided with a tapering guide 88 protruding therefrom as it extends from hinge portion 98 towards distal end 90. Guide 88 is received within a recess 86 defined in second arm 84. Vertebral spacer 80 also defines tool receiving opening 99 defined in hinge 98. Tool receiving opening 99 is configured to have an internal thread to accommodate an insertion tool, such as tool 300 illustrated in FIG. 17.

Figure 15:
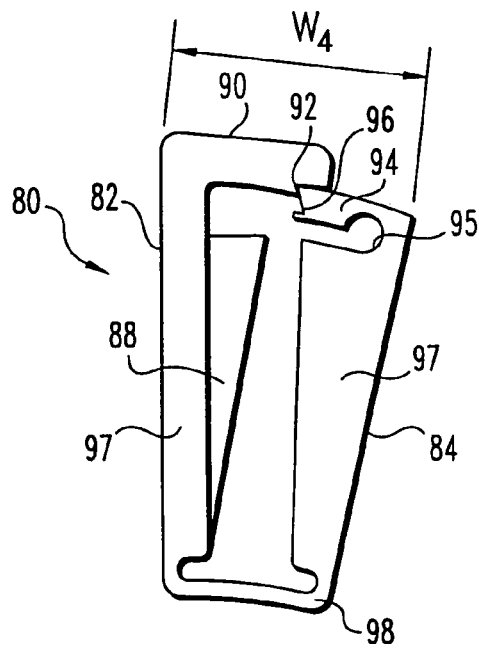
FIG. 15 is a top plan view of the vertebral spacer device of FIG. 13 in an expanded position.
Figure 16:
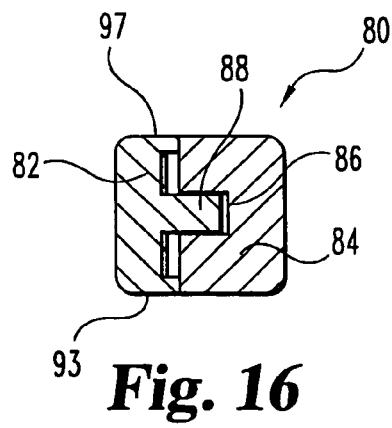
FIG. 16 is a cross-sectional view of the vertebral spacer device of FIG. 14 taken along line 16-16.

Second arm 84 includes a locking arm 94 adjacent its distal end that is integrally formed with laterally expandable portion 84 via locking arm hinge portion 95. Locking arm 94 is configured to be positioned adjacent distal end portion 90 in the closed position shown in FIG. 14. In the closed position the device is in a reduced size configuration suitable for insertion. In this configuration, device 80 has a lateral width $W_3$ extending transverse to the longitudinally axis of the device. Preferably, spacer 80 is formed of an at least partially resilient material and distal end portion 90 may be biased toward cavity 85. In this configuration the arms tend to move to the locked position once the spacer is sufficiently expanded. Distal end portion 90 includes a catch 92 formed thereon, and locking arm 94 includes a catch-receiving portion 96. When the device 80 is laterally expanded to a second lateral position, as shown in FIG. 15, locking arm hinge 95 urges locking arm 94 towards distal end portion 90 until catch-receiving portion 94 engages catch 92. Catch 92 prevents displacement of expandable portion 84 towards main body portion 82 after the device 80 is inserted in the disc space. The device 80 is then held in the expanded position, and cavity 85 may be packed with bone growth material through opening 99. Further openings for bone ingrowth or bone growth material packing may be provided. In the laterally expanded configuration of FIG. 15, device 80 has a maximum lateral width $W_4$, width $W_4$ being greater than $W_3$.

It should be noted that the device 80 defines a top vertebral bearing surface 97 and a bottom vertebral bearing surface 93. The bearing surfaces 93 and 97 are composed of the surfaces provided on first arm 82, second arm 84, and hinge 98. In a preferred embodiment, bearing surfaces 93 and 97 are spaced apart a height that remains relatively constant from the closed to expanded positions. The bearing surfaces contact the adjacent vertebrae endplates to provide an even distribution of loads through the endplates and balanced loading conditions. While not shown, it will be understood that these surfaces may include roughening to inhibit expulsion.

It is contemplated that devices according to the present invention may be manufactured from bio-compatible materials having at least some flexibility without fracture. Further, it is anticipated that portions of bone may be used provided the hinge points have been at least partially demineralized to provide flexibility. Demineralization of bone is known in the art and will not be described further herein. More preferably, device 80 is formed from material having a degree of resiliency tending to urge locking arm 94 into the locking position with the catch 92 engaged with catch-receiving portion 94. Such materials may include, but are not limited to, stainless steel, shape memory alloys, composites and plastics. Moreover, while flexible hinge portions have been disclosed, it will be understood that hinge pin and channel connections may replace the flexible hinges without deviation from the spirit of the invention. Optionally, a biasing mechanism, such as a spring, may be placed between the arms to urge the device to the expanded configuration.

Figure 17:
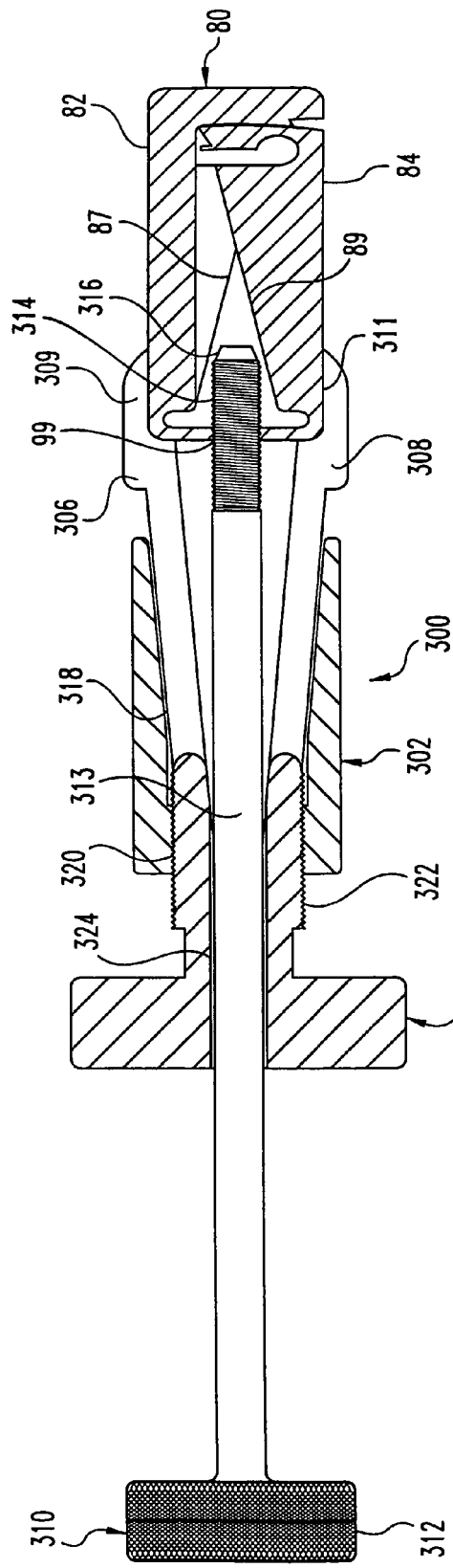
FIG. 17 is a partial cross-sectional side view of an insertion tool device usable with the vertebral spacer device of FIG. 13.

The present invention also contemplates an instrument for inserting and expanding an implant according to the present invention. Referring now to FIG. 17, an insertion tool 300 is illustrated. Tool 300 includes a hollow outer sleeve 302 that receives a portion of an inner sleeve 304. Inner sleeve 304 defines connecting portion 322 that engages mating portion 320 of outer sleeve 302. In the illustrated embodiment, inner sleeve 304 is threadedly received within the outer sleeve 302. Inner sleeve 304 further defines an opening 324 therethrough for receiving rod 310. Inner sleeve 304 also includes a pair of movable arms 306 and 308 having gripping portions 309 and 311, respectively, configured for holding device 80 during insertion. In order for arms 306 and 308 to grip the device 80, outer 302 is moved with respect to inner handle 304 such that inclined portion 318 of outer sleeve 302 urges gripping portions 309 and 311 of arms 306 and 308 against device 80. In the illustrated device 300, this accomplished by rotating outer handle 302 about a thread on connecting portion 322 towards the device 80.

Once device is engaged by gripping portions 309 and 311, it may be inserted into the disc space. After insertion of device 80 to the desired location, rod 310 is operable to laterally expand device 80. Rod 310 has a handle portion 312, and opposite a threaded portion 314, and a shaft 313 extending therebetween. In a preferred embodiment, shaft 313 has a distal end 316 that is beveled to engage the inclined surfaces 87 and 89 of first arm 82 and second arm 84, respectively. Handle 310 may be engaged with device 80 during insertion into the disc space via threaded engage with tool receiving opening 99. The threaded engagement between threaded portion 314 and the device 80 allows the device 80 to be positioned within the disc space. In order to position the device 80 to its expanded configuration, mechanism 310 is threaded within receiving portion 99 in order to urge distal end 316 against surfaces 87 and 89 to laterally expand device 80 to the expanded or second lateral configuration as shown in FIG. 15.

Figure 13:
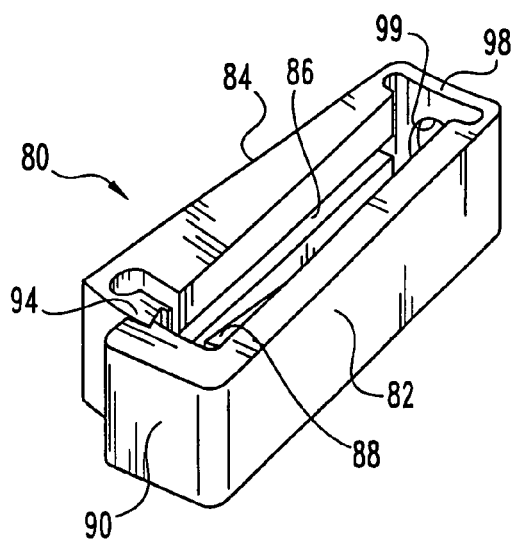
FIG. 13 is a perspective view of an alternate embodiment vertebral spacer device according to the present invention.
Figure 14:
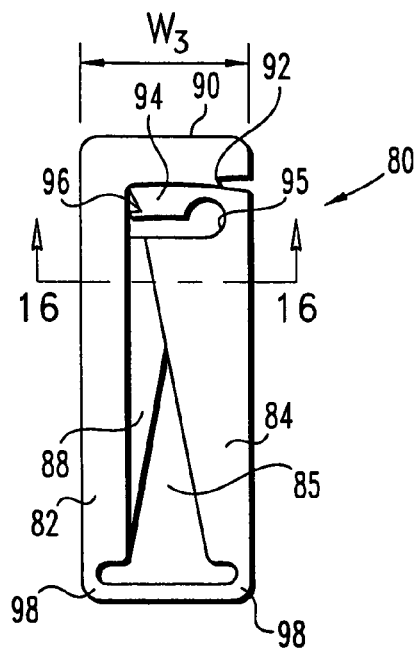
FIG. 14 is a top plan view of the vertebral spacer device of FIG. 13 in an unexpanded position.

While the above-described spacer embodiments of FIGS. 1 and 13 have been described as having a first arm and a second arm movable coupled, it will be understood that the invention contemplates a main body portion and laterally expandable portion movably coupled thereto. Specifically, while first arm and second arm may simultaneously move laterally to form the expanded configuration, it is contemplated that one arm may remain stationary while the other arm moves. Moreover, the device may be formed such that the device includes a stationary main body with one or more movable laterally expandable portions movable to give the device both a reduced size configuration and a laterally expanded size configuration.

Figure 18A:
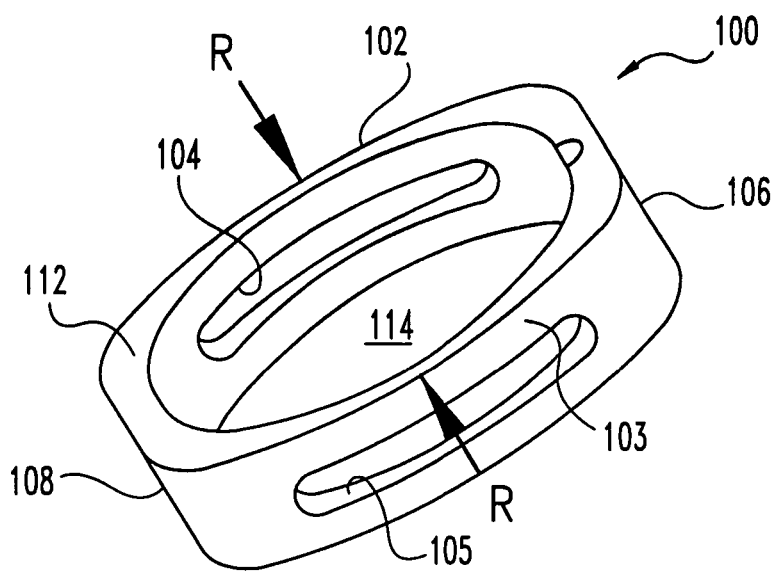
FIG. 18a is a perspective view of another embodiment of a vertebral spacer device according to the present invention.
Figure 18B:
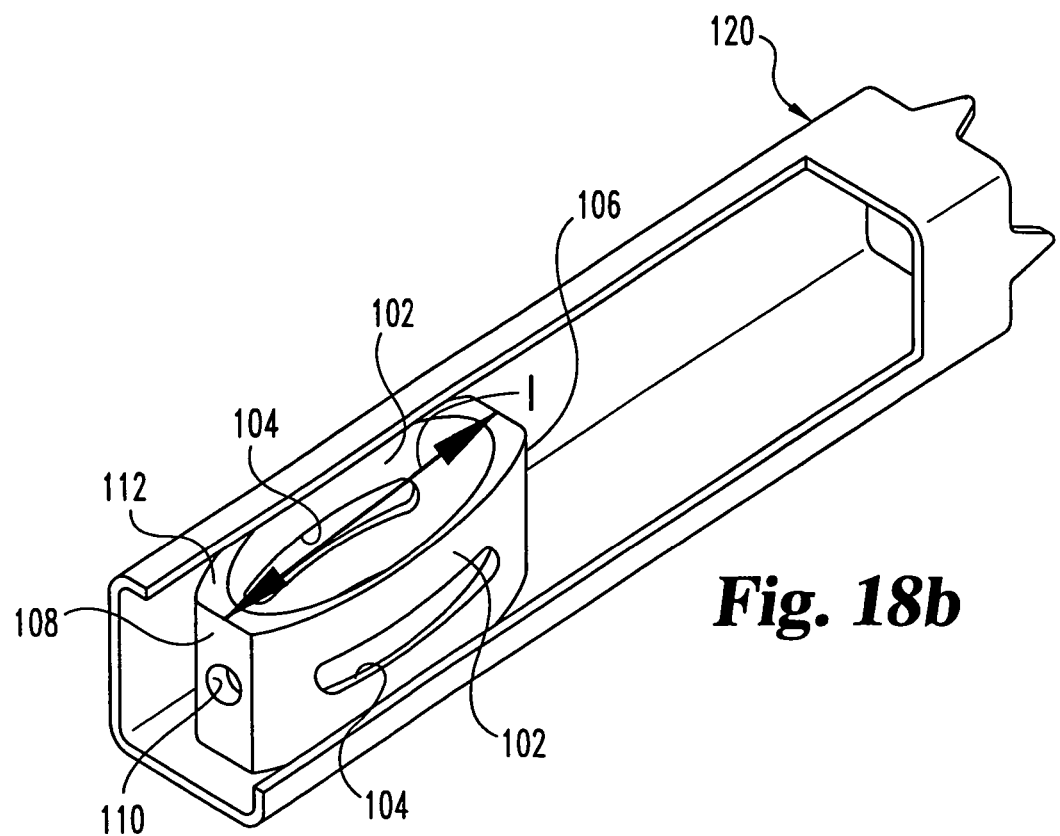
FIG. 18b is a perspective view of the vertebral spacer device of FIG. 18a constrained within a delivery system.

Referring now to FIGS. 18a and 18b, another embodiment of the present invention is illustrated. Vertebral spacer device 100 includes a pair of lateral arms 102 and 103 extending between a distal end 106 and a proximal end 108. The device 100 includes a top vertebral bearing surface 112 and an identical bottom vertebral bearing surface (not shown). A central cavity 114 is formed between the lateral arms 102. The device 100 also includes openings 104 and 105 defined by lateral arms 102 and 103, respectively. Openings 104 and 105 permit communication between the interior and exterior of the device and reduce the material in walls 102 and 103, thereby increasing the flexibility of device 100. Device 100 also includes at least one insertion tool opening 110 formed in proximal end 108. Preferably, opening 110 is threaded to receive a correspondingly threaded insertion tool (not shown).

The embodiment of FIG. 18 is preferably formed of a resiliently flexible material. Such materials may include, without limitation, bio-compatible metals (including shape memory alloys), composites, and plastics. In a preferred embodiment, the device 100 is expanded and contracted by making the device 100 from a shape memory material, such as nitinol, exhibiting super elasticity and/or temperature induced shape memory. The device 100 is initially formed in a laterally expanded or second position. In order to insert the device 100 through a small opening and into the disc space, it is contracted to a first lateral position by applying a force to lateral arms 102 and 103 in the direction indicated by the arrows "R". Thus, the device is laterally compressed into a smaller sized configuration. Often, the device will experience some elongation, as shown by dimension "I". When the device is contracted, as shown in FIG. 19, it may be inserted through a tubular delivery system, such as the cannula 120. Once the device is inserted in the disc space, it is no longer confined by the cannula 120, and it self-expands laterally to a second position within the disc space approximating its pre-insertion condition. Cavity 114 may be filled with bone growth material delivered through opening 110. Cavity 114 may also be partially loaded with bone growth material prior to insertion. It is also contemplated herein that device 100 may be inserted into the disc space without use of cannula 120, such as by an open surgical procedure. Temporary compression may be achieved by an external device such as, but without limitation, pliers adapted to compress the implant.

Figure 19A:
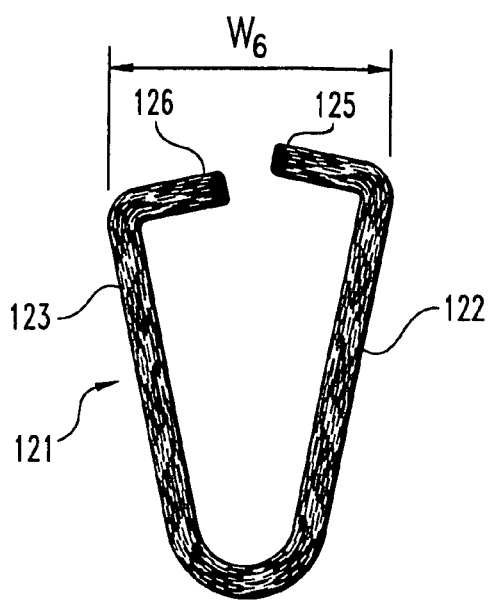
FIG. 19a is a top view of a laterally expandable implant according to another embodiment of the present invention.
Figure 19B:
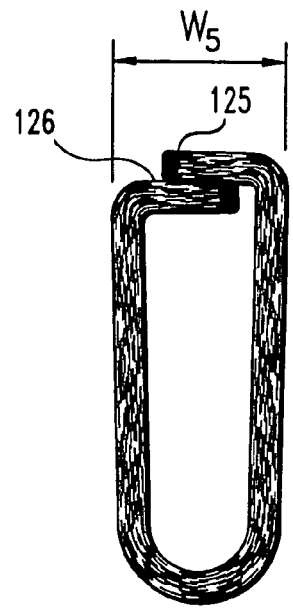
FIG. 19b is a top view of the implant of FIG. 19a in a compressed configuration.
Figure 19C:
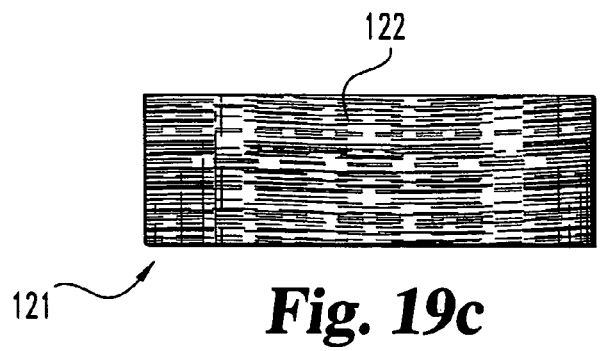

FIGS. 19a through 19c illustrate a further embodiment of a laterally expandable spacer according to the present invention. Spacer 121 includes arms 122 and 123 connected by a flexible portion. Arm 122 terminates in an end wall 125 and arm 123 terminates in an end wall 126. As shown in FIG. 19b, the respective lengths of arms 122 and 123 allow end wall 126 to nest within end wall 125.

Spacer 121 is preferably formed of a flexible and resilient material. The spacer is in a relaxed form in the expanded configuration of FIG. 19a having a lateral width $W_6$. Width $W_6$ is decreased to lateral width $W_5$ by the application of compressive force on arms 122 and 123 urging end walls 125 and 126 towards one another. Preferably, spacer 121 self-expands from the reduced size configuration of FIG. 19b to the expanded configuration of 19a. Preferably $W_6$ is approximately twice $W_5$, although a greater or lesser amount of lateral expansion may be provided. Preferably, spacer 121 is formed of a fiber reinforced polymer composite. The fibers, shown by the parallel shading marks in FIGS. 19a through 19c, extend generally parallel to the length of side walls 122 and 123. It will be understood that this arrangement of fibers provides a degree of flexibility between the arms but resists compression from the upper to lower surfaces engaging the vertebral bodies.

Figure 20A:
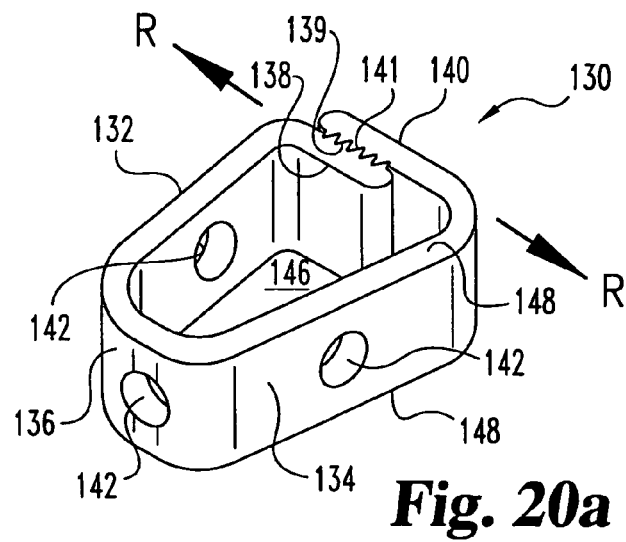
FIG. 20a is a perspective view of another embodiment of a vertebral spacer device according to the present invention.

Referring to FIG. 20a, another embodiment of a vertebral spacer device is illustrated. Vertebral spacer device 130 includes a first arm 132 and a second arm 134 fixedly connected via hinge portion 136. In this embodiment, hinge portion 136 is integrally formed with first arm 132 and second arm 134. First arm 132 includes first lateral extending portion 138, and second arm 134 includes a second laterally extending portion 140. First laterally extending portion 138 includes first serrations 139 and second laterally extending portion 140 includes corresponding second serrations 141 disposed adjacent first serrations 139. Serrations 139 and 141 cooperate in interdigiting fashion to restrain lateral contracting of the first arm 132 with respect to the second arm 134. The device 130 also includes tool opening 142, which allows engagement of device 130 to insertion and/or expansion tools. As previously disclosed, opening 142 may be threaded to receive a corresponding threaded tool. As with earlier disclosed embodiments, device 130 also defines a cavity 146, and includes substantially planar vertebral bearing surfaces 148 and 149 for engaging respective end plates of adjacent vertebrae.

The device 130 is shown in a contracted position, and once inserted the device may be expanded by applying a force in the direction of the arrows "R". The interdigiting serrations 139 and 141 must yield sufficiently to allow movement of first arm 132 with respect to second arm 134, while maintaining the separation of arm 132 and second arm 134 when the force is removed.

Figure 20B:
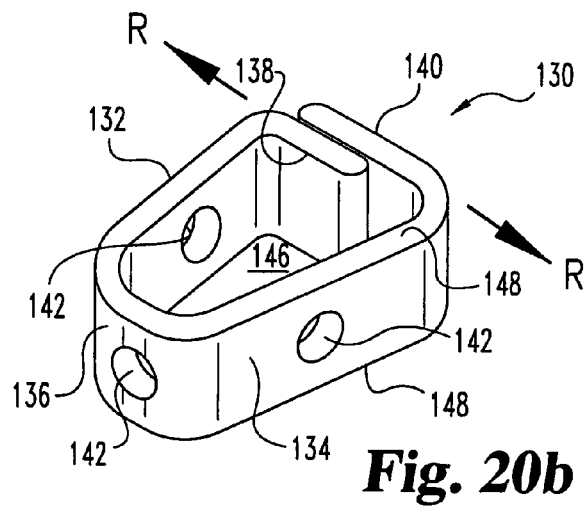
FIG. 20b is a perspective view of the space device of FIG. 20a without the ratchet mechanism.

FIG. 20b represents a modified version of FIG. 20a lacking serrations 139 and 141. Preferably, spacer 130 is formed of a flexible material that may be plastically deformed. Thus, force applied to arms 132 and 134 to expand the device plastically deforms hinge portion 136. Plastic deformation of hinge portion 136 maintains the device in the expanded condition.

Figure 21:
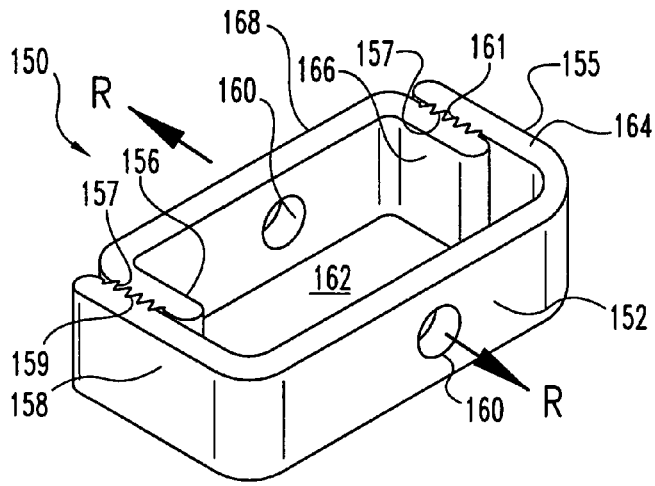
FIG. 21 is a perspective view of yet another embodiment of a vertebral spacer device according to the present invention.

FIG. 21 illustrates another embodiment of the vertebral spacer device of the present invention. Device 150 includes a first arm 152 and a second arm 154. The term arm as used throughout the disclosure is used broadly to define sections and portions of devices. Arms may not necessarily move within a device configuration. First arm 152 includes a first extension 158 and a second extension 155. Second arm 154 includes third extension 156 and fourth extension 166. First arm 152 is sized to receive extensions 156 and 166 within extensions 158 and 155. First extension 158 defines first serrations 159 and second extension defines second serrations 161. Third extension 156 defines third serrations 157 and fourth extension 166 defines fourth serrations 168. First serrations 159 and third serrations 157 cooperate in interdigiting fashion in cooperation with interdigiting engagement of second serrations 161 and fourth serrations 168 to maintain lateral spacing between first arm 152 and second arm 154. Device 150 also defines an upper vertebral engaging surface 164, and an identical lower vertebral engaging surface, and tool openings 160. Device 150 also defines a cavity 162, which may be filled with bone growth material. Once the device 150 is inserted into the disc space, it may be expanded by applying force in the direction indicated by arrow "R" to move first arm 152 with respect to second arm 154.

Figure 22:
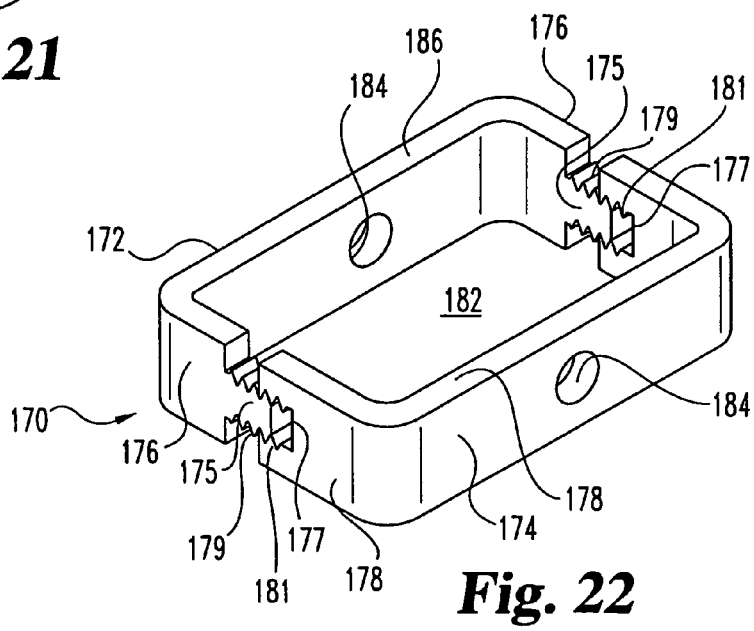
FIG. 22 is a perspective view of yet another embodiment of a vertebral spacer device according to the present invention.

Referring now to FIG. 22, yet another embodiment of a vertebral spacer device in accordance with the present invention is illustrated. Device 170 includes a first arm 172 and a second arm 174. First arm 172 includes first a pair of extensions 176 and second arm 174 includes a pair of extensions 178. Extensions 176 include projections 175, and extensions 178 define receptacles 177. Projections 175 are configured to be placed within a respective one of receptacles 177. Projections 178 define first serrations 179 thereon, and receptacle 177 define second serrations 181 thereon. First serrations 179 and second serrations 181 cooperate in interdigiting fashion to resist displacement at first arm 172 with respect to second arm 174. However, first serrations 179 and second serrations 181 yield sufficiently to allow lateral expansion of the device 170. Device 170 includes an upper vertebral engaging surface 186 and an identical lower vertebral engaging surface. Arms 172 and 174 define a central cavity 182 for receiving bone growth material.

A tool 340 for expanding the devices illustrated in FIGS. 20-22 is illustrated in FIGS. 23 and 23a. Tool 340 includes a first lever 350 pivotably coupled to a second lever 360 by pin 346. First lever 350 includes a first handle portion 351 pivotably coupled to a first extension 353 via pin 352. Second lever 360 has a second handle portion 361 pivotably coupled to a second extension 363 via pin 362. Extensions 353 and 363 are pivotable engaged via pin 348. Handle 340 also includes ratchet mechanism 342 coupled to one of the handle portions 351, 361. In the illustrated embodiment, ratchet mechanism 342 is coupled to second handle portion 361 via pin 344. Ratchet mechanism 342 has teeth 346 for engaging first handle portion 351. Ratchet mechanism 342 is operable to maintain the relative spacing between handle portions 351 and 361 when engaged thereto.

First extension 353 has a first engagement portion 354 and second extension 363 has a cooperable second engagement portion 364 located at respective distal ends of each extension 353 and 363. First engagement portion 354 includes a first coupling 356, and second engagement portion 364 includes a second coupling 366, each for coupling respective lever arms 350 and 360 to a vertebral spacer device, such as device 150 illustrated in FIG. 21. Couplings 356 and 366 extend through a corresponding one of tool openings 160 to engage the device 150. As shown in detail in FIG. 23a with respect to first engagement portion 354, first and second couplings 356 and 366 each include a first and second head 358 and 368 and a first and second recess 359 and 369, positioned between first and second extensions 353 and 363, respectively. The first and second recesses 359 and 369 are configured to receive a portion of the arms 152 and 154 therein to allow head 358 and 368 to engage the device 150. The device 150 may then be laterally expanded or contracted as needed by manipulation of first and second lever arms 351 and 361. Tool 340 may then be uncoupled from device 150 by withdrawing the first and second coupling 356 and 366 from device 150.

Figure 24:
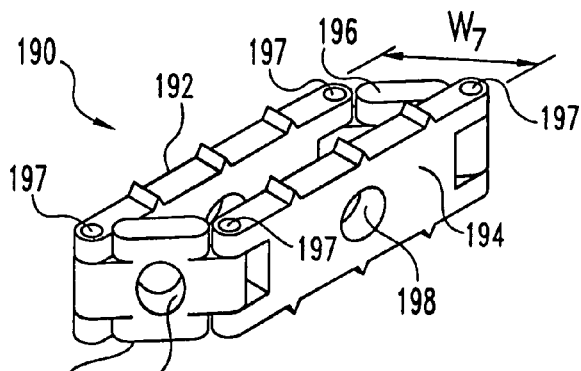
FIG. 24 is a perspective view of another embodiment of a vertebral spacer device according to the present invention shown in a collapsed position.
Figure 24A:
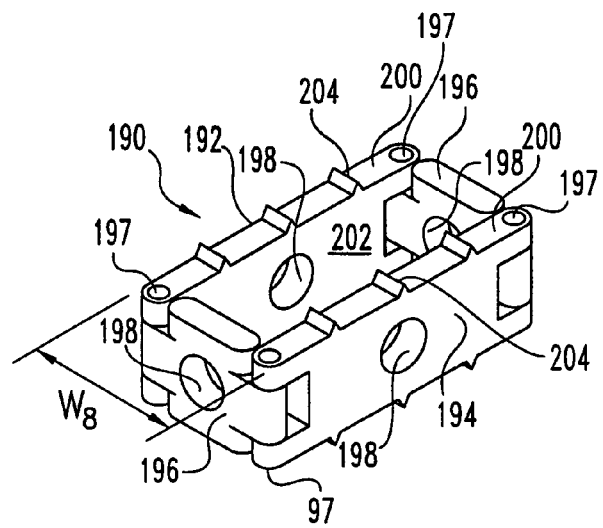
FIG. 24a is a perspective view of the vertebral spacer device of FIG. 22 shown in an expanded position.

Referring now to FIGS. 24-24a, another embodiment of a vertebral spacer device according to the present invention is illustrated. Device 190 includes first arm 192 and second arm 194. First arm 192 is pivotally coupled to second arm 194 via monolithic sidewalls 196 extending therebetween. In the illustrated embodiment, two monolithic sidewalls 196 are shown with one at the proximal end of the device 190 and the other sidewall 196 at the distal end of device 190. The first and second arms 192 and 194 are engaged to sidewalls 196 via hinge pins 197. The device 190 also defines an upper vertebral engaging surface 200 and a lower vertebral engaging surface, and tool insertion openings 198. In one embodiment, the device 190 is provided with ridges 204 extending from vertebral engaging surfaces for engaging the adjacent vertebral endface plates. A central cavity 202 for receipt of bone growth material is defined by the sidewalls 96, first arm 192, and second arm 194.

As shown in FIG. 24, the device 190 is collapsible to a first reduced size configuration for insertion into the disc space having a lateral width $W_7$. Once the device is inserted, it may be pivoted about hinge portions 197 to an expanded position having greater width $W_8$ as shown in FIG. 24a. The device may be expanded by a tool inserted through one or more of the openings 198. Bone growth material may be placed in cavity 202 through openings 198.

Figure 25:
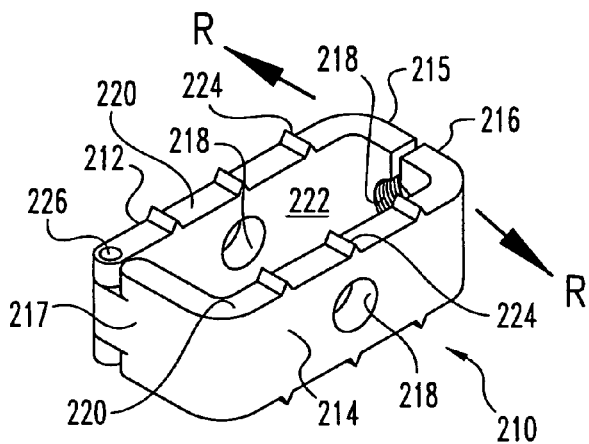
FIG. 25 is a perspective view of yet another embodiment of a vertebral spacer device according to the present invention.

Another embodiment of the vertebral spacer device of the present invention is illustrated in FIG. 25. The vertebral spacer device 210 includes a first arm 212 and a second arm 214. First arm 212 includes a first laterally extending portion 215, and second arm 214 includes a second laterally extending portion 216. Second arm 214 also includes offset portion 217 extending to engage first arm 212 at connection 226. Preferably, connection 226 is a hinge-type connection. The device 210 also includes vertebral engagement surfaces 220 and 221 and, in a preferred embodiment, ridges 224 for engaging vertebral endface plates after insertion. A central cavity 222 is formed between first arm 212 and second arm 214. Bone growth material may be placed in central cavity 222. Openings 218 may also be provided in the device for receiving various tools for inserting and expanding the device. A force applied in the direction indicated by the arrows "R" will act to expand the device 210 from the first reduced size lateral position of FIG. 25 to a second expanded lateral position (not shown) after insertion of the device 210 into the disc space.

The vertebral spacers of the present invention may be placed and maintained in position within the disc space by additional fixation. The vertebral spacer devices are generally retained in position by the compressive forces of the vertebral bodies acting on the bone engaging surfaces of the implant. The spacer devices are preferably configured to transmit the compressive forces from the upper vertebral body directly through a one-piece monolithic side wall to the lower vertebral body and to limit concentration of compressive loads at the movable couplings of the arms. Moreover, it is contemplated herein that fixation devices may be used in conjunction with the vertebral spacer device of the present invention. Alternatively, the vertebral spacer devices may be provided with an opening for receiving a fixation device, such as a bone screw, allowing the vertebral spacer to be attached to adjacent vertebrae. Moreover, it is contemplated that the bone engaging surfaces may be configured, without limitation, to be tapered, concave or convex in order to approximate the disc space. More specifically, upper and lower bone engaging surfaces may define an angle therebetween for enhancing lordosis of the spine.

Preferably, implants according to the present invention may have lengths varying from 20 mm to 26 mm. Further, implants may have reduced size insertion configurations with widths varying preferably between 16 mm and 20 mm. Although these dimensions may be used, larger or smaller dimensions may be used without deviating from the scope of the invention.

While the invention has been illustrated and described in detail in the drawings and foregoing description, the same is to be considered as illustrative and not restrictive in character, it being understood that only the preferred embodiment has been shown and described and that all changes and modifications the come within the spirit of the invention are desired to be protected.

What is claimed is:

1. An apparatus, comprising a vertebral spacer insertable between adjacent vertebrae having:
   a first monolithic arm having a proximal end and a distal end;
   a second monolithic arm having a proximal end and a distal end;
   a first monolithic sidewall having a first end pivotally connected to the proximal end of the first arm and a second end pivotally connected to the proximal end of the second arm to allow the first and second ends of the first sidewall to pivot about the proximal ends of the first and second arms; and
   a second monolithic sidewall having a first end pivotally connected to the distal end of the first arm and a second end pivotally connected to the distal end of the second arm to allow the first and second ends of the second sidewall to pivot about the distal ends of the first and second arms; and
   wherein the spacer is collapsible to a reduced size configuration defining a first overall lateral spacer width between the first and second arms for insertion into a disc space and the spacer is expandable to an expanded configuration inside the disc space to define a second overall lateral spacer width between the first and second arms greater than the first overall lateral spacer width, the expanded configuration providing the spacer with an increased lateral base of support within the disc space, and wherein the first arm, the second arm and the first and second sidewalls are rigid and substantially non-deformable in both the reduced size and expanded configurations and as the spacer is expanded from the reduced size configuration to the expanded configuration.

2. The apparatus of claim 1, further comprising hinge pins; and
   the first end of the first sidewall is pivotally connected to the proximal end of the first arm by a first hinge pin, and the second end of the first sidewall is pivotally connected to the proximal end of the second arm by a second hinge pin; and
   wherein the first end of the second sidewall is pivotally connected to the distal end of the first arm by a third hinge pin, and the second end of the second sidewall is pivotally connected to the distal end of the second arm by a fourth hinge pin.

3. The apparatus of claim 1, wherein the first arm, the second arm, the first sidewall, and the second sidewall define a central cavity for receiving bone growth material.

4. The apparatus of claim 3, further comprising the bone growth material received in the central cavity.

5. The apparatus of claim 3, wherein the first arm defines a tool insertion opening through which the bone growth material is inserted into the central cavity.

6. The apparatus of claim 1, wherein the spacer defines one or more tool insertion openings for expanding the spacer.

7. The apparatus of claim 1, wherein the expanded configuration of the spacer comprises a substantially rectangular configuration.

8. The apparatus of claim 1, wherein the reduced size configuration and the expanded configuration of the spacer each generally define a parallelogram.

9. An apparatus, comprising a vertebral spacer insertable between adjacent vertebrae having:
   a first monolithic arm having a proximal end and a distal end;
   a second monolithic arm having a proximal end and a distal end;
   a first monolithic sidewall having a first end pivotally connected to the proximal end of the first arm and a second end pivotally connected to the proximal end of the second arm to allow the first and second ends of the first sidewall to pivot about the proximal ends of the first and second arms; and
   a second monolithic sidewall having a first end pivotally connected to the distal end of the first arm and a second end pivotally connected to the distal end of the second arm to allow the first and second ends of the second sidewall to pivot about the distal ends of the first and second arms; and
   wherein the spacer is collapsible to a reduced size configuration defining a first overall lateral spacer width between the first and second arms for insertion into a disc space and the spacer is expandable to an expanded configuration inside the disc space to define a second overall lateral spacer width between the first and second arms greater than the first overall lateral spacer width, the expanded configuration providing the spacer with an increased lateral base of support within the disc space, and wherein the first arm, the second arm and the first and second sidewalls are rigid and substantially non-deformable; and wherein the spacer defines upper and lower vertebral engaging surfaces comprising upper and lower longitudinal edges of the first and second arms; and wherein the upper and lower longitudinal edges defined by each of the first and second arms define a height of the spacer and are provided with ridges for engaging adjacent vertebral end face plates; and wherein the height of the spacer in the expanded configuration is substantially the same as the height of the spacer in the reduced size configuration.

10. The apparatus of claim 9, wherein the reduced size configuration and the expanded configuration of the spacer each generally define a parallelogram.

11. An apparatus, comprising:
a vertebral spacer insertable between adjacent vertebrae having a proximal end and a distal end, the vertebral spacer including:
a first arm having a proximal end and a distal end,
a second arm having a proximal end and a distal end,
two monolithic sidewalls pivotally coupling the first arm to the second arm, and
wherein a first of the two monolithic sidewalls is positioned at the proximal end of the vertebral spacer and has a first end pivotally connected to the proximal end of the first arm and a second end pivotally connected to the proximal end of the second arm to allow the first and second ends of the first sidewall to pivot about the proximal ends of the first and second arms, and
wherein a second of the two monolithic sidewalls is positioned at the distal end of the vertebral spacer and has a first end pivotally connected to the distal end of the first arm and a second end pivotally connected to the distal end of the second arm to allow the first and second ends of the second sidewall to pivot about the distal ends of the first and second arms, and
wherein the first arm, the second arm, and the two sidewalls each comprise monolithic elements that cooperate to define a cavity for receiving bone growth material, and
wherein the vertebral spacer is collapsible to a reduced size configuration having a first width for insertion into a disc space, wherein the vertebral spacer pivots to an expanded configuration having a second width that is larger than the first width once inserted into the disc space, and wherein the first arm, the second arm and the two sidewalls are rigid and substantially non-deformable in both the reduced size and expanded configurations and as the spacer is expanded from the reduced size configuration to the expanded configuration.

12. The apparatus of claim 11, wherein the vertebral spacer defines upper and lower vertebral engaging surfaces comprising upper and lower longitudinal edges of the first and second arms; and
wherein the upper and lower longitudinal edges defined by each of the first and second arms define a height of the spacer and are provided with ridges for engaging adjacent vertebral end face plates; and
wherein the height of the spacer in the expanded configuration is substantially the same as the height of the spacer in the reduced size configuration.

13. The apparatus of claim 11, wherein the reduced size configuration and the expanded configuration of the spacer each generally define a parallelogram.

14. An apparatus, comprising a vertebral spacer insertable between adjacent vertebrae having:
a first monolithic arm having a proximal end and a distal end;
a second monolithic arm having a proximal end and a distal end;
a first monolithic sidewall having a first end pivotally connected to the proximal end of the first arm and a second end pivotally connected to the proximal end of the second arm to allow the first and second ends of the first sidewall to pivot about the proximal ends of the first and second arms, and
a second monolithic sidewall having a first end pivotally connected to the distal end of the first arm and a second end pivotally connected to the distal end of the second arm to allow the first and second ends of the second sidewall to pivot about the distal ends of the first and second arms; and
wherein the first arm, the second arm and the sidewalls define vertebral engaging surfaces configured to engage adjacent vertebral end face plates; and
wherein the spacer is collapsible to a reduced size configuration defining a first overall lateral spacer width for insertion into a disc space and is expandable to an expanded configuration inside the disc space having a substantially rectangular shape and defining a second overall lateral spacer width greater than the first overall lateral spacer width, the expanded configuration providing the spacer with an increased lateral base of support within the disc space, and wherein the first arm, the second arm and the first and second sidewalls are rigid and substantially non-deformable in both the reduced size and expanded configurations and as the spacer is expanded from the reduced size configuration to the expanded configuration.

15. The apparatus of claim 14, wherein the first arm defines a tool insertion opening.

16. The apparatus of claim 14, further comprising hinge pins; and
wherein the first end of the first sidewall is pivotally connected to the proximal end of the first arm by a first hinge pin, and the second end of the first sidewall is pivotally connected to the proximal end of the second arm by a second hinge pin; and
wherein the first end of the second sidewall is pivotally connected to the distal end of the first arm by a third hinge pin, and the second end of the second sidewall is pivotally connected to the distal end of the second arm by a fourth hinge pin.

17. The apparatus of claim 14, wherein the reduced size configuration and the expanded configuration of the spacer each generally define a parallelogram.

18. An apparatus, comprising a vertebral spacer insertable between adjacent vertebrae having:
a first monolithic arm having a proximal end and a distal end;
a second monolithic arm having a proximal end and a distal end;
a first monolithic sidewall having a first end pivotally connected to the proximal end of the first arm and a second end pivotally connected to the proximal end of the second arm to allow the first and second ends of the first sidewall to pivot about the proximal ends of the first and second arms, and
a second monolithic sidewall having a first end pivotally connected to the distal end of the first arm and a second end pivotally connected to the distal end of the second arm to allow the first and second ends of the second sidewall to pivot about the distal ends of the first and second arms; and wherein the first arm, the second arm and the sidewalls define vertebral engaging surfaces configured to engage adjacent vertebral end face plates; and wherein the vertebral engaging surfaces comprise upper and lower longitudinal edges of the first and second arms; and wherein the upper and lower longitudinal edges defined by each of the first and second arms define a height of the spacer and each have ridges to engage the adjacent vertebral end faces; and wherein the spacer is collapsible to a reduced size configuration defining a first overall lateral spacer width for insertion into a disc space and is expandable to an expanded configuration inside the disc space having a substantially rectangular shape and defining a second overall lateral spacer width greater than the first overall lateral spacer width, the expanded configuration providing the spacer with an increased lateral base of support within the disc space, and wherein the height of the spacer in the expanded configuration is substantially the same as the height of the spacer in the reduced size configuration.

19. The apparatus of claim 18, wherein the reduced size configuration and the expanded configuration of the spacer each generally define a parallelogram.

20. An apparatus, comprising a vertebral spacer insertable between adjacent vertebrae having:
  a first monolithic arm having a proximal end and a distal end;
  a second monolithic arm having a proximal end and a distal end;
  a first monolithic sidewall having a first end pivotally connected to the proximal end of the first arm and a second end pivotally connected to the proximal end of the second arm to allow the first and second ends of the first sidewall to pivot about the proximal ends of the first and second arms; and
  a second monolithic sidewall having a first end pivotally connected to the distal end of the first arm and a second end pivotally connected to the distal end of the second arm to allow the first and second ends of the second sidewall to pivot about the distal ends of the first and second arms; and
  wherein the first and second arms of the spacer each include upper and lower longitudinal edges that define upper and lower vertebral engaging surfaces configured to engage adjacent vertebrae, the upper and lower longitudinal edges of the first and second arms define a height of the spacer and are each provided with ridges for engaging adjacent vertebral end face plates; and
  wherein the spacer is collapsible to a reduced size configuration defining a first overall lateral spacer width between the first and second arms for insertion into a disc space and the spacer is expandable to an expanded configuration inside the disc space to define a second overall lateral spacer width between the first and second arms greater than the first overall lateral spacer width, the expanded configuration providing the spacer with an increased lateral base of support within the disc space, and wherein the height of the spacer in the expanded configuration is substantially the same as the height of the spacer in the reduced size configuration.

21. The apparatus of claim 20, wherein the reduced size configuration and the expanded configuration of the spacer each generally define a parallelogram.

22. An apparatus, comprising a vertebral spacer insertable between adjacent vertebrae having:
  a first monolithic arm having a proximal end and a distal end;
  a second monolithic arm having a proximal end and a distal end;
  a first monolithic sidewall having a first end pivotally connected to the proximal end of the first arm and a second end pivotally connected to the proximal end of the second arm to allow the first and second ends of the first sidewall to pivot about the proximal ends of the first and second arms; and
  a second monolithic sidewall having a first end pivotally connected to the distal end of the first arm and a second end pivotally connected to the distal end of the second arm to allow the first and second ends of the second sidewall to pivot about the distal ends of the first and second arms; and
  wherein the spacer is collapsible to a reduced size configuration defining a first overall lateral spacer width between the first and second arms for insertion into a disc space and the spacer is expandable to an expanded configuration inside the disc space to define a second overall lateral spacer width between the first and second arms greater than the first overall lateral spacer width, the expanded configuration providing the spacer with an increased lateral base of support within the disc space, and wherein the reduced size configuration and the expanded configuration of the spacer each generally define a parallelogram.

23. An apparatus, comprising a vertebral spacer insertable between adjacent vertebrae having:
  a first monolithic arm having a proximal end and a distal end;
  a second monolithic arm having a proximal end and a distal end;
  a first monolithic sidewall having a first end pivotally and movably coupled to the proximal end of the first arm and a second end pivotally and movably coupled to the proximal end of the second arm to allow the first and second ends of the first sidewall to pivot about the proximal ends of the first and second arms; and
  a second monolithic sidewall having a first end pivotally and movably coupled to the distal end of the first arm and a second end pivotally and movably coupled to the distal end of the second arm to allow the first and second ends of the second sidewall to pivot about the distal ends of the first and second arms; and
  wherein the spacer is collapsible to a reduced size configuration defining a first overall lateral spacer width between the first and second arms for insertion into a disc space and the spacer is expandable to an expanded configuration inside the disc space to define a second overall lateral spacer width between the first and second arms greater than the first overall lateral spacer width, the expanded configuration providing the spacer with an increased lateral base of support within the disc space; and
  wherein the spacer has an overall height in the expanded configuration that is substantially the same as the overall height of the spacer in the reduced size configuration; and
  wherein the first arm, the second arm and the first and second sidewalls are rigid and substantially non-deformable in both the reduced size and expanded configurations and as the spacer is expanded from the reduced size configuration to the expanded configuration.

24. The apparatus of claim 23, wherein the reduced size configuration and the expanded configuration of the spacer each generally define a parallelogram.

25. An apparatus, comprising:
a vertebral spacer insertable between adjacent vertebrae having a proximal end and a distal end, the vertebral spacer including:
a first arm having a proximal end and a distal end,
a second arm having a proximal end and a distal end,
two monolithic sidewalls pivotally coupling the first arm to the second arm, and
   wherein a first of the two monolithic sidewalls is positioned at the proximal end of the vertebral spacer and has a first end pivotally connected to the proximal end of the first arm and a second end pivotally connected to the proximal end of the second arm to allow the first and second ends of the first sidewall to pivot about the proximal ends of the first and second arms, and
   wherein a second of the two monolithic sidewalls is positioned at the distal end of the vertebral spacer and has a first end pivotally connected to the distal end of the first arm and a second end pivotally connected to the distal end of the second arm to allow the first and second ends of the second sidewall to pivot about the distal ends of the first and second arms, and
wherein the first arm, the second arm, and the two sidewalls each comprise monolithic elements that cooperate to define a cavity for receiving bone growth material, and wherein the first arm, the second arm and the two sidewalls are rigid and substantially non-deformable; and
wherein the spacer is collapsible to a reduced size configuration defining a first overall lateral spacer width between the first and second arms for insertion into a disc space, and the spacer is expandable to an expanded configuration inside the disc space to define a second overall lateral spacer width between the first and second arms greater than the first overall lateral spacer width, wherein the expanded configuration provides the spacer with an increased lateral base of support within the disc space, and wherein the reduced size configuration and the expanded configuration of the spacer each generally define a parallelogram.

26. An apparatus, comprising:
a vertebral spacer insertable between adjacent vertebrae having a proximal end and a distal end, the vertebral spacer including:
a first arm having a proximal end and a distal end,
a second arm having a proximal end and a distal end,
two monolithic sidewalls pivotally coupling the first arm to the second arm, and
   wherein a first of the two monolithic sidewalls is positioned at the proximal end of the vertebral spacer and has a first end pivotally and movably coupled to the proximal end of the first arm and a second end pivotally and movably coupled to the proximal end of the second arm to allow the first and second ends of the first sidewall to pivot about the proximal ends of the first and second arms, and
   wherein a second of the two monolithic sidewalls is positioned at the distal end of the vertebral spacer and has a first end pivotally and movably coupled to the distal end of the first arm and a second end pivotally and movably coupled to the distal end of the second arm to allow the first and second ends of the second sidewall to pivot about the distal ends of the first and second arms, and
wherein the first arm, the second arm, and the two sidewalls each comprise monolithic elements that cooperate to define a cavity for receiving bone growth material, and
wherein the spacer is collapsible to a reduced size configuration defining a first overall lateral spacer width between the first and second arms for insertion into a disc space, and the spacer is expandable to an expanded configuration inside the disc space to define a second overall lateral spacer width between the first and second arms greater than the first overall lateral spacer width, wherein the expanded configuration provides the spacer with an increased lateral base of support within the disc space, wherein the spacer has an overall height in the expanded configuration that is substantially the same as the overall height of the spacer in the reduced size configuration; and
wherein the first arm, the second arm and the first and second sidewalls are rigid and substantially non-deformable in both the reduced size and expanded configurations and as the spacer is expanded from the reduced size configuration to the expanded configuration.

27. The apparatus of claim 26, wherein the reduced size configuration and the expanded configuration of the spacer each generally define a parallelogram.

28. An apparatus, comprising a vertebral spacer insertable between adjacent vertebrae having:
a first monolithic arm having a proximal end and a distal end;
a second monolithic arm having a proximal end and a distal end;
a first monolithic sidewall having a first end pivotally and movably coupled to the proximal end of the first arm and a second end pivotally and movably coupled to the proximal end of the second arm to allow the first and second ends of the first sidewall to pivot about the proximal ends of the first and second arms; and
a second monolithic sidewall having a first end pivotally and movably coupled to the distal end of the first arm and a second end pivotally and movably coupled to the distal end of the second arm to allow the first and second ends of the second sidewall to pivot about the distal ends of the first and second arms; and
wherein the spacer is collapsible to a reduced size configuration defining a first overall lateral spacer width for insertion into a disc space and is expandable to an expanded configuration inside the disc space having a substantially rectangular shape and defining a second overall lateral spacer width greater than the first overall lateral spacer width, the expanded configuration providing the spacer with an increased lateral base of support within the disc space;
wherein the spacer has an overall height in the expanded configuration that is substantially the same as the overall height of the spacer in the reduced size configuration; and
wherein the first arm, the second arm and the first and second sidewalls are rigid and substantially non-deformable in both the reduced size and expanded configurations and as the spacer is expanded from the reduced size configuration to the expanded configuration.

29. The apparatus of claim 28, wherein the reduced size configuration and the expanded configuration of the spacer each generally define a parallelogram.

* * * * *